United States Patent [19]

King et al.

[11] Patent Number: 5,120,847

[45] Date of Patent: Jun. 9, 1992

[54] PROCESS FOR IODINATING OR BROMINATING THE α-METHYLENIC CARBON OF A SECONDARY AMIDE

[75] Inventors: Anthony O. King, Hillsboro; Sandor Karady, Mountainside; Kevin Anderson, Plainsboro; Newton L. Abramson, Edison; Richard F. Shuman, Westfield, all of N.J.

[73] Assignee: Merck & Co., Inc., Rahway, N.J.

[21] Appl. No.: 572,920

[22] Filed: Aug. 27, 1990

[51] Int. Cl.$^5$ .................... A61K 31/395; C07J 51/00
[52] U.S. Cl. ...................... 546/77; 540/523; 540/530; 540/485; 564/151
[58] Field of Search .............. 546/77; 540/485, 523, 540/530; 564/151

[56] References Cited

U.S. PATENT DOCUMENTS

| | | | |
|---|---|---|---|
| 4,036,831 | 7/1977 | Loken | 260/239.5 |
| 4,220,775 | 9/1980 | Rasmusson et al. | 546/77 |
| 4,377,584 | 3/1983 | Rasmusson et al. | 424/258 |
| 4,760,071 | 7/1988 | Rasmusson et al. | 514/284 |
| 4,859,681 | 8/1989 | Rasmusson et al. | 514/284 |
| 5,021,575 | 6/1991 | King et al. | 546/77 |

FOREIGN PATENT DOCUMENTS

0004949A1 10/1979 European Pat. Off.
0155096A3 9/1985 European Pat. Off.
0298652A2 1/1989 European Pat. Off.
2018257A 10/1979 United Kingdom.

OTHER PUBLICATIONS

Bhattacharya et al, Silylation-mediated oxidation ... J. Am. Chem. Soc. 110 No. 10, 3318 (1988).
Back, T. G. Oxidation J. Org. Chem. 46, 1442 (1981).
Magnus P. and Pappalardo, P. A. J. Am. Chem. Soc. 108 212 (1986).
Rasmusson et al, J. Med. Chem. 29, 2298 (1986).
Trost and Salzmann J. Am. Chem. Soc. 95:20, 6840 (1973).

Primary Examiner—Nicholas S. Rizzo
Attorney, Agent, or Firm—Charles M. Caruso; William H. Nicholson; Gerard H. Bencen

[57] ABSTRACT

A novel, facile, and specific process for α-iodinating or α-brominating the α-methylenic carbon of a straight chain, branched chain, or cyclic secondary amide, such as a lactam or an azasteroid, comprises reacting the amide with trialkylsilyl-X ($R_3Si-X$), where X is Br, I, or Cl, and R is methyl, ethyl, or n-propyl, in the presence of $I_2$ or $Br_2$. The α-iodo- or α-bromo-amide is useful for making the α,β-unsaturated amide through dehydrohalogenation.

7 Claims, No Drawings

PROCESS FOR IODINATING OR BROMINATING THE α-METHYLENIC CARBON OF A SECONDARY AMIDE

BACKGROUND OF THE INVENTION

The novel process of this invention is particularly useful for preparing an intermediate α-iodo-, or α-bromo-amide which is readily dehydrohalogenated to an α,β-unsaturated amide.

Where the amide is a saturated azasteroid, this novel process greatly facilitates the production of the Δ-1 azasteroid which is useful as a potent inhibitor of testosterone 5-α-reductase [see Nayfe et al., *Steroids*, 14, 269 (1969); Voigt and Hsia, *Endocrinology*, 92, 1216 (1973); Canadian Pat. No. 970,692]. In this regard, known methods for introduction of the Δ-1 double bond into azasteroids include selenic anhydride oxidation [Back, T. G., *J. Org. Chem.*, 46, 1442 (1981); Rasmussen et al., *J. Med. Chem.* 29, 2298 (1986)], sulfoxide elimination [U.S. Pat. Nos. 4,377,584; 4,220,775], a complicated 5-step dehydrogenation involving a sulfenate intermediate [Magnus et al., *J. Am. Chem. Soc.* 108, 221 (1986)], and silylation mediated DDQ (2,3-dichloro-5,6-dicyano-1,4-benzoquinone) oxidation [Bhattacharya et al., *J. Am. Chem. Soc.* 110, 3318 (1988)].

The process of the instant invention avoids some of the disadvantages present in the prior art methods which include poor yields, expensive reagents, unwanted by-products, and the use of toxic selenium catalysts.

SUMMARY OF THE INVENTION

The novel process of this invention is a facile and specific process for α-iodinating or α-brominating an α,β-saturated straight chain, branched chain, or cyclic amide, such as a lactam or an azasteroid. The process comprises reacting the amide with trialkylsilyl-X ($R_3Si—X$), where X is Br, I, or Cl, and R is methyl, ethyl, or n-propyl, in the presence of $I_2$ or $Br_2$, to yield the α-iodo- or α-bromo-amide. These products are useful for making the α,β-unsaturated amide through dehydrohalogenation. Thus, in a preferred embodiment of the invention, where the starting amide is an α-β saturated azasteroid, this process provides a means for obtaining the α-iodo- or α-bromo-azasteoid. These products may be dehydrohalogenated by methods known in the art to form the Δ-1-azasteroid which is useful as a potent inhibitor of 5-α-reductase.

Accordingly, it is an object of this invention to provide a process for α-iodinating or α-brominating an α,β-saturated straight chain, branched chain, or cyclic amide, such as a lactam and preferably an azasteroid, the products of which are useful as starting materials for making α,β-unsaturated amides.

DETAILED DESCRIPTION OF THE INVENTION

The novel process of this invention comprises reacting α-methylenic carbon of a secondary amide with trialkylsilyl-X, $R_3Si—X$, where X is I, Br, or Cl, and R is methyl, ethyl, or n-propyl, in the presence of $I_2$ or $Br_2$. The α-iodinated or α-brominated products of this process may then be used to make an α,β-unsaturated amide through known methods of dehydrohalogenation. The process is shown in Scheme 1:

SCHEME 1

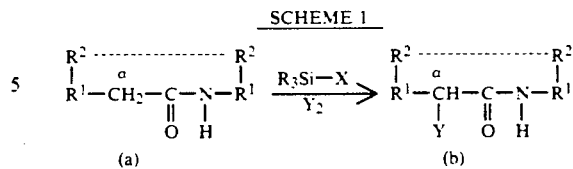

wherein:
X is:
a) I,
b) Br, or
c) Cl;
Y is:
a) I, or
b) Br;
$R^1$ is:
a) $—(CH_2)_{1-5}—$,
b) -aryl-,
c) $—(CH_2)_{1-5}$-aryl-,
d) —(meta or para)-substituted aryl-, or
e) $—(CH_2)_{1-5}$-aryl-, wherein the aryl is a substituted aryl;
$R^2$ is hydrogen, or optionally joined together to form:
a) $—(CH_2)_{1-5}—$,
b) -substituted lower alkyl
c) -aryl-,
d) -substituted aryl-, or
e)

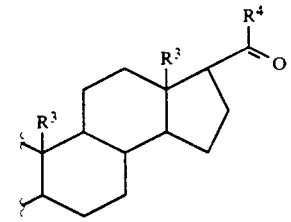

wherein
$R^3$ is:
a) -hydrogen, or
b) $—R^5$; and
$R^4$ is:
a) —OH,
b) $—OR^5$, or
c) $—NHR^5$; and
$R^5$ is lower alkyl of between 1 and 5 carbon atoms.

Lower alkyl means straight or branched chain alkyls containing from 1 to 5 carbons; aryl includes phenyl or naphthyl; substituted alkyl or aryl means an alkyl or aryl substituted with one or two substituents selected from among: $—R^5$, $—OR^5$, $—CO_2R^5$, $—NR^5_2$, $—CONR^5_2$, $—CONHR^5$, $—CO$-aryl, $—SR^5$, -halogen. $R_3Si—X$ is the trialkylsilyl-X mediator, with X and R as defined above.

Thus, in one embodiment of the invention $R^2$ is hydrogen and the straight chain amide, 1-s of Scheme 2 below, is converted into the α-iodo- or α-bromo-amide II-s.:

SCHEME 2

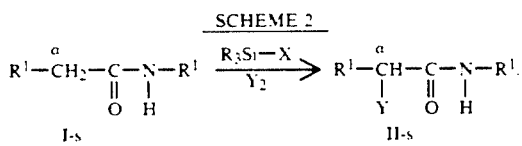

wherein X, Y, and $R^1$ are as defined above.

In another embodiment of the invention, $R^2$ is present and the lactam I-l of Scheme 3 below is converted into the α-iodo- or α-bromo-lactam II-l:

SCHEME 3

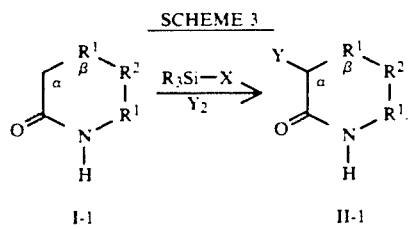

wherein X, Y, $R^1$ and $R^2$ are as defined above.

In a preferred embodiment of the process of this invention the starting amide is a 3-keto 4-azasteroid. This process has been optimized and, as shown in Scheme 4 below, application of this process to a compound of formula I-a generates a compound of formula II-a. II-a is useful for making a Δ-1 azasteroid, useful as an inhibitor of 5-α-reductase, through dehydrohalogenation of II-a:

SCHEME 4

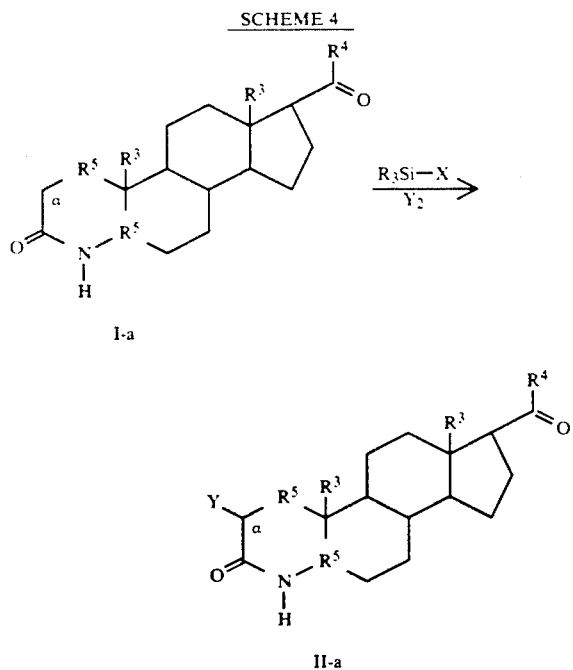

wherein X and Y are as previously defined and:

$R^3$ is:
a) -hydrogen, or
b) —$R^5$; and $R^4$ is:
a) —$OR^5$,
b) —NH—$R^5$, or
c) —OH.

The conditions described hereinbelow are optimized for azasteroid amides (see Example 3), but are applicable to lactams and secondary amide containing compounds in general. The TMSX mediator is included in the reaction at between 0.5 and 10 molar equivalents, and preferrably at an equimolar amount, as compared with azasteroid. TMSCl is commercially available and relatively inexpensive. TMSI is easily produced in situ by inclusion of about a 2-fold molar excess of $I_2$ in reactions incorporating TMSCl as the mediator. For brominated products, either TMSBr or TMSI may be used as the mediator with about a 2- to 5-fold molar excess of $Br_2$. However, in this case, complete conversion of starting material into product requires the presence of some iodine, with the ratio between iodine to bromine determining the ratio of 2-bromo to 2-iodo product obtained (see example 3).

The reaction is run under an inert atmosphere, such as nitrogen, at a temperature ranging from −20° C. to room temperature, and preferrably between −15° C. and 0° C. Appropriate solvents include toluene, methylene chloride, and tetrahydrofuran (THF). Addition of a base, such as N,N,N',N'-tetramethylethylenediamine (TMEDA), triethylamine ($Et_3N$) or diethylmethylamine ($Et_2MeN$), whose hydrohalide salts are poorly soluble in the above solvents, increases the conversion of I-a into II-a. The progress of the reaction should be monitored, usually from 30 minutes and up to 3 hours being required, and the reaction is quenched by addition of aqueous sodium sulfite upon completion.

Upon isolation of the 2-bromo or 2-iodo azasteroid II-a, it is possible to generate the Δ-1 azasteroid III-a by a dehydrohalogenation reaction. This is accomplished by addition of about a ten-fold molar excess of a suitable base such as tetrabutylammonium fluoride, or preferably potassium tert-butoxide (see Example 2).

Presented in Example 1 is the TMSCl-mediated iodination of an azasteroid in the presence of $I_2$ to provide the 2-iodo-4-azasteroid in high yield. This product may be utilized in the synthesis of other functional groups of choice. For instance, in Example 2, the product from Example 1 is converted into the active Δ-1-olefin inhibitor of 5-α-reductase. Example 3 presents, in tabular form, different conditions for achieving brominated or iodinated azasteroids. As shown by the iodination of seven-membered lactams in Examples 4 and 5, the process herein described is not restricted to iodination of six-membered or steroidal lactams. In addition, Example 7 exemplifies the process as applied to a straight chain amide. These examples are provided to further define but not to limit the scope of this invention.

EXAMPLE 1

2-iodo-3-oxo-4-aza-5-α-androstane-17 β-N-(1,1-Dimethylethyl)-carboxamide 20.0 Grams ($5.3 \times 10^{-2}$ mole) of α-aza steroid amide, 200 ml of toluene and 25.0 ml ($1.7 \times 10^{-1}$ mole) of tetraethyl ethylene diamide (TMEDA) was cooled with stirring under nitrogen to −15° C. and 13.5 ml ($1.1 \times 10^{-1}$ mole) of TMSCl was added. The slurry was stirred for 5 min and 20.5 g ($8.1 \times 10^{-2}$ mole) of iodine was added. The reaction was warmed to 0° C. and checked for completion by HPLC.

The reaction was quenched with 100 ml of 10% sodium sulfite and 13% sodium chloride at 0° C. and the phases were separated. The organic phase was diluted with 100 ml isopropyl alcohol and washed with a second 100 ml of 10% sodium sulfite and 13% sodium chloride, followed by 100 ml of 13% sodium chloride.

The combined aqueous phases were back-extracted with 20 ml of 33% isopropyl alcohol in toluene and the organic phases combined. The volume of organic phases was reduced in vacuo with heating to 40 ml and 100 ml of hexanes was added slowly at room temperature with stirring. The crystallized solid was filtered and dried in vacuo at 60° C. to yield the slightly orange title compound.

$^1$H NMR (CDCl$_3$) δ 7.04 (s, 1H), 5.09 (s, 1 H), 4.71 (dd, J=10.5, 8.1 Hz, 1 H), 3.11 (dd, J=12.3, 3.2 Hz, 1 H), 2.52 (dd, J=13.6, 8.1 Hz, 1 H), 2.20-1.75 (m, 4 H), 1.75-1.45 (m, 5 H), 1.45-1.10 (m, 5 H), 1.28 (s, 9 H), 1.10-0.70 (m, 3 H), 0.81 (s, 3H), 0.61 (S, 3 H).

EXAMPLE 2

3-Oxo-4-aza-5-α-androst-1-ene-17-β-N-(1,1-Dimethylethyl)-carboxamide 8.0 Grams (7.0×10$^{-2}$ mole) of potassium t-butoxide was dissolved in 20 ml of dry DMF with stirring and the solution cooled to −10° C. A solution of 3.5 g (7.1×10$^{-3}$ mole) of 2-iodo-α amide in 15 ml of dry DMF was added dropwise. The mixture was stirred vigorously for 10 minutes and the reaction was quenched with the drop-wise addition of 7.2 ml (7.1×10$^{-2}$ mole) of acetic acid at below 10° C.

The reaction was stirred for 5 minutes and 200 ml of 21% sodium chloride was added slowly at 0° C. resulting in the crystallization of the steroid. The reaction was stirred overnight at 0° C. The sample was isolated by filtration and dried in a vacuum oven at 60° C. to give 2.5 g of an off-white solid of 93.3 wt % purity. Recrystallization from isopropyl acetate gave the title compound.

EXAMPLE 3

Iodination and Bromination of 4-Aza-5-α-Androstan-3-one-Derivatives

In order to optimize reaction conditions, several parameters were altered and the resultant yield of brominated or iodinated azasteroid obtained is shown in TABLE I:

TABLE I

Iodination and Bromination of 4-Aza-5-α-Androstan-3-one Derivatives.

| | Molar Equivalents | | | | Ratio (LC area %) | | |
|---|---|---|---|---|---|---|---|
| Run | R$^4$ | TMEDA | TMSX | I$_2$ | Br$_2$ | SM | 2-Br | 2-I |
| 1 | —NHtBu | 5 | Br, 5 | — | 5 | 50 | 50 | — |
| 2 | —NHtBu | 5 | I, 1 | — | 5 | — | 90 | 10 |
| 3 | —NHtBu | 5 | I, 1 | — | 2 | — | 22 | 78 |
| 4 | —NHtBu | 5 | I, 1 | 2 | — | — | — | 100 |
| 5 | —NHtBu | 5 | I, 0.2 | 2 | — | 25 | — | 75 |
| 6 | —NHtBu | 5 | Cl, 1 | 1.5 | — | 20 | — | 80 |
| 7 | —NHtBu | 3 | Cl, 2 | 1.5 | — | — | — | 100$^a$ |
| 8 | —NHtBu | 3 | Cl, 2 | 1.5 | — | — | — | 100$^b$ |
| 9 | —NHtBu | 4 | Cl, 3 | 2.5 | — | — | — | 100$^c$ |
| 10 | —OMe | 5 | I, 0.5 | 2 | — | — | — | 100 |
| 11 | —OMe | 3 | Cl, 2 | 2 | — | — | — | 100$^d$ |
| 12 | —NHtBu | $e$ | Cl, 3 | 2 | — | — | — | 100 |
| 13 | —OH | $f$ | Cl, 3 | 2 | — | 0.8 | — | 99.2 |
| 14 | —NHtBu | $g$ | Cl, 3 | 2 | — | 59 | — | 41 |
| 15 | —OH | 5 | Cl, 4 | 3 | — | 2 | — | 98 |

(Reactions were run in CH$_2$Cl$_2$ unless otherwise noted)
Legend to Table 1:
SM = starting material. —NHtBu = tertiary butyl amine; —OMe = methoxy; —OH = hydroxyl;
$^a$95% isolated.
$^b$in toluene, 0° C.;
$^c$in THF, −10° C.,
$^d$96% isolated.
$^e$4 molar equivalents triethylamine used;
$^f$4 equivalents diethylmethylamine used;
$^g$4 equivalents diisopropylethylamine used.

As shown in TABLE I, as little as 0.5 molar equivalents of TMSI was sufficient to catalyze the complete iodination of I when R=—OMe (Run #10). The halogenation reaction performed equally well in methylene chloride, toluene and tetrahydrofuran solvents (Runs #7, 8, 9). N,N,N'N'-Tetramethylethylenediamine (TMEDA, Runs #1-11 and 15), triethylamine (Et$_3$N, Run #12) and diethylmethylamine (Et$_2$MeN, Run #14) were found to be suitable bases for this reaction.

Surprisingly, diisopropylethylamine in methylene chloride gave a 59:41 mixture of starting material:2-iodo product (Run #14), and only a trace of the 2-iodo product was observed in toluene under similar conditions. The low solubility of the hydrohalide salts of TMEDA, Et$_3$N and Et$_2$MeN in the above solvents may be responsible for their usefulness as opposed to the poor results with diisopropylethylamine. Precipitation of these hydrohalide salts may remove sufficient acid from the reaction so that the equilibrium is displaced toward product allowing the reaction to proceed to completion.

The presence of iodide in the reaction mixture is crucial for the reaction to reach 100% conversion. Using 5 equivalents of TMSBr and 5 equivalents of bromine, the reaction never reached 100% conversion but gave a 50:50 mixture of starting material:2-bromo product (Run #1). However, by adjusting the amount of TMSI and bromine, it was possible to control the ratio of 2-bromo versus 2-iodo products formed. Using 1 equivalent of TMSI and 5 equivalents of bromine, the 2-bromo product:2-iodo product ratio was 90:10 (Run #2). Dropping the amount of bromine to 2 equivalents gave a 2-bromo:2-iodo ratio of 22:78 (Run #3). One could obtain 100% 2-iodo product by using 1 equivalent of TMSI and 2 equivalents of iodine (Run #4). Further decreasing the TMSI to 0.2 equivalent while maintaining the iodine at 2 equivalents gave only 75% conversion to the 2-iodo product under similar conditions (Run #5).

It was also possible to generate TMSI in situ from TMSCl and iodine. A slightly greater amount of TMSCl is needed, however, than when TMSI is used alone. With 1 equivalent of TMSCl and 1.5 equivalents of iodine, the reaction only proceeded to 80% conversion (Run #6), but 100% conversion was obtained by increasing TMSCl to 2 equivalents while maintaining the iodine at 1.5 equivalents (Run #7). Ester and carboxylic acid functional groups at the C-17 position could be tolerated in the reaction, and afforded the corresponding 2-iodo analogs in excellent yields (runs #10, 11). No dihalogenation was observed.

EXAMPLE 4

TMSI Mediated Production of α-Iodo-ε-Caprolactam

ε-Caprolactam (1.78 g, 1.57×10⁻² moles) and TMEDA (12.0 ml, 7.95×10⁻² mole) were dissolved in 60 ml dry CH₂Cl₂ and cooled to −10° C. under an atmosphere of nitrogen. TMSI (6.9 ml, 4.85×10⁻² mole) was added slowly and the mixture was stirred for 15 minutes. The temperature of the reaction was maintained at −10° C. and I₂ (6.0 g, 2.31×10⁻² mole) was added all at once. The reaction was run for 30 minutes at −10° C. and quenched with sodium sulfite (100 ml, 10% aqueous solution). The layers were separated and the CH₂Cl₂ phase was washed with 20 ml of 1.2 N HCl. The CH₂Cl₂ was separated, dried, and removed to give the title compound as a slightly yellow product.

¹H NMR (300 MHz). 6.44 (s, 1H), 4.75-4.88 (m, 1H), 3.38-3.60 (m, 1H), 3.10-3.34 (m, 1H), 1.78-2.06 (m, 4H), 1.37-1.78 (m, 2H).

EXAMPLE 5

TMSI Mediated Production of
3-iodo-2,3,4,5-Tetrahydro-1-H-[1-(benzazepin-2-one)]

2,3,4,5-Tetrahydro-1-H-[1-(benzazepin-2-one)] (0.1 g, 6.2×10⁻⁴ mole) and TMEDA (0.5 ml, 3.3×10⁻³ mole) were dissolved in dry CH₂Cl₂ and cooled to −10° C. under an atmosphere of nitrogen. TMSI (0.18 ml, 1.26×10⁻³ mole) was added slowly and the mixture was stirred for 15 minutes. The temperature of the reaction was maintained at −10° C. and I₂ (0.24 g, 9.2×10⁻⁴ mole) was added all at once. The reaction was run for 30 minutes at −10° C. and quenched with sodium sulfite (5 ml, 10% aqueous solution). The layers were separated and the CH₂Cl₂ phase was washed with 5 ml of 1.2N HCl. The CH₂Cl₂ was separated, dried, and removed to give the title compound as a white solid product.

¹H NMR (300 M Hz). 8.50 (s 1H), 7.12-7.40 (m, 3H), 7.07 (d, J=7.7 Hz, 1H), 4.70 (t, J=8.7 Hz, 1H), 2.90-3.12 (m, 1H), 2.59-2.90 (m, 3H).

EXAMPLE 6

2-iodo-3-oxo-4-aza-5α-andtostane-17β-carboxylic acid

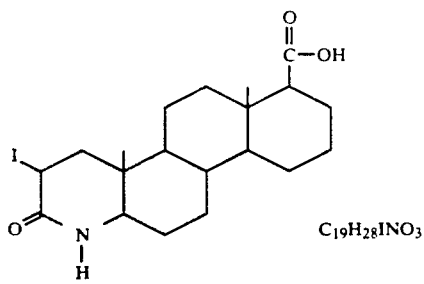

C₁₉H₂₈INO₃

To a suspension of 3-oxo-4-aza-5α-androstane-17β-carboxylic acid (1 gram, 3.13 mmole) in toluene (20 ml) was added tetramethyl-ethylenediamina (1.8 ml, 12 mmole) and trimethylsilyl chloride (1.14 ml, 9 mmole). After stirring at room temperature for one hour the solution was cooled in an ice bath. Iodine (1.51 g, 6 mmole) was added and the mixture agitated with cooling for 6 hrs. Extraction of the toluene solution with 10% aqueous sodium bisulfite solution, followed by acidification with 1N hydrochloric acid precipitated the product which was recovered by filtration. Following washing with toluene and acetonitrile, 1.3 g of the title compound was recovered as colorless crystals. The structure was confirmed by NMR and FAB-MS.

¹H NMR (CD₃CO₂D) δ 4.96 (dd, J=10.0, 8.3 Hz, 1H), 3.21 (dd, J=12.4, 3.5 Hz, 1H), 2.62 (dd, J=13.6, 8.2 Hz, 1H), 2.43 (t, J=9.6 Hz, 1H), 2.20-1.91 (m, 3H), 1.91-1.64 (m, 4H), 1.64-0.98 (m, 10H), 0.98-0.79 (m, 1H), 0.88 (s, 3H), 0.73 (s, 3H).

EXAMPLE 7

N-4-methylbenzyl-2-iodo-propionamide

Following essentially the procedure given in Example 4 above but starting with the straight chain N-4-methylbenzyl-propionamide, the title compound was generated.

¹H NMR (300 M Hz). 7.16 (dd, J=11.3 Hz, 8.4 Hz, 4H), 4.47 (q, J=7.0, 1H), 4.30-4.46 (m, 2H), 2.34 (s, 3H), 1.98 (d, J=7.0 Hz, 3H).

EXAMPLE 8

Methyl-2-iodo-3-oxo-4-Aza-5α-Androstane-17β-carboxylate

Following essentially the procedure given in Example 4, the title compound was prepared.

¹H NMR: (CDCl₃) δ 6.99 (s, 1 H), 4.74 (dd, J=10.5, 8.0 hz, 1 H), 3.63 (s, 3 H), 3.14 (dd, J=12.4, 3.4 Hz, 1 H), 2.56 (dd, J=13.6, 8.1 Hz, 1 H), 2.32 (t, J=9.1 Hz, 1 H), 2.2-1.90 (m, 3 H), 1.90-1.57 (m, 4 H), 1.57-0.53 (m, 9 H), 0.84 (s, 3 H), 0.62 (s, 3 H).

What is claimed is:

1. A process for iodinating or brominating the α-methylenic carbon of a secondary amide which comprises reacting the secondary amide with R₃Si—X, wherein X is I, Br, or Cl, and R is methyl, ethyl, or n-propyl, in the presence of I₂ or Br₂, in an aprotic organic solvent, selected from among toluene, methylene chloride, and tetrahydrofuran, in the presence of a base, selected from among TMEDA, Et₃N, and Et₂MeN, and isolating the iodinated or brominated product, wherein said secondary amide reactant and said product have the structures (a) and (b) respectively:

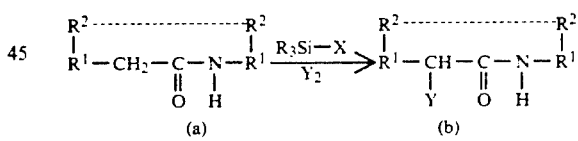

wherein:
X is:
a) I,
b) Br, or
c) Cl;
Y is:
a) I, or
b) Br;
R¹ is:
a) —(CH₂)₁₋₅—,
b) -aryl-,
c) —(CH₂)₁₋₅-aryl-,
d) -(meta or para)-substituted aryl-, or
e) —(CH₂)₁₋₅-aryl-, wherein the aryl is a substituted aryl;
R² is hydrogen, or optionally joined together to form:
a) —(CH₂)₁₋₅—,
b) -substituted lower alkyl-,
c) -aryl-, d) -substituted aryl-, or e)

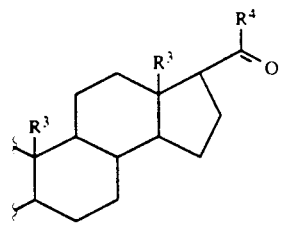

wherein

R³ is:

a) -hydrogen, or b) —R⁵;

R⁴ is:

a) —OH, b) —OR⁵, or c) —NHR⁵;

R⁵ is a lower alkyl of one to five carbons; a substituted aryl or substituted lower alkyl comprises aryl or alkyl substituted with one or two substituents selected from among: —R⁵, —OR⁵, —CO₂R⁵, —NR₂⁵, —CONR₂⁵, —CONHR⁵, —CO-aryl, —SR⁵, -halogen; alkyl is a straight or branched chain of 1 to 5 carbons; and aryl comprises phenyl or napthyl.

2. The process of claim 1, wherein R² is hydrogen, which comprises making the product II-s from the reactant I-s according to the Scheme:

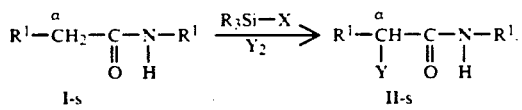

3. The process of claim 1 for preparing a compound of structure II-1 from a lactam of structure I-1 according to the scheme:

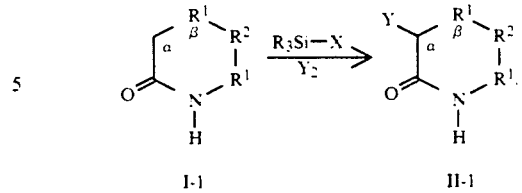

4. The process of claim 1 for preparing a compound of structure II-a from a 3-keto-4-azasteroid of structure I-a:

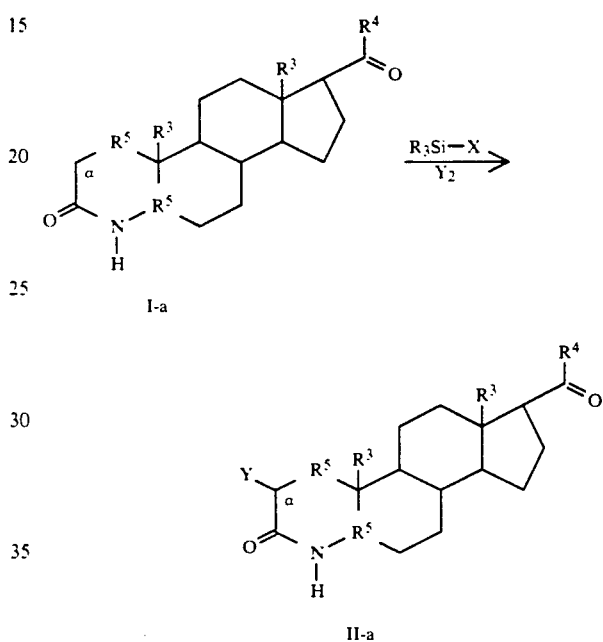

wherein:

R³ is:

a) -hydrogen, or b) —R⁵; and

R⁴ is:

a) —OR⁵, b) —NH—R⁵, or c) —OH.

5. The process of claim 4 wherein —R⁵— is —CH—, —R³ is —CH₃, and —R⁴ is —OCH₃, or —OH.

6. The process of claim 5 wherein R⁴ is —NH-tertiary butyl.

7. The process of claim 4 where Y is iodo-, which comprises the additional step of treating the compound II-a with a base to generate the Δ-1 unsaturated azasteroid.

* * * * *